(12) United States Patent
Graalfs et al.

(10) Patent No.: US 8,673,988 B2
(45) Date of Patent: Mar. 18, 2014

(54) GRAFT COPOLYMERS FOR ION EXCHANGE CHROMATOGRAPHY

(75) Inventors: Heiner Graalfs, Ober-Ramstadt (DE); Lothar Britsch, Reute (DE)

(73) Assignee: Merck Patent GmbH, Darmstadt (DE)

( * ) Notice: Subject to any disclaimer, the term of this patent is extended or adjusted under 35 U.S.C. 154(b) by 269 days.

(21) Appl. No.: 13/055,983

(22) PCT Filed: Jul. 8, 2009

(86) PCT No.: PCT/EP2009/004952
§ 371 (c)(1),
(2), (4) Date: Jan. 26, 2011

(87) PCT Pub. No.: WO2010/012358
PCT Pub. Date: Feb. 4, 2010

(65) Prior Publication Data
US 2011/0136925 A1    Jun. 9, 2011

(30) Foreign Application Priority Data
Jul. 30, 2008  (EP) ..................................... 08013674

(51) Int. Cl.
*B01J 41/20*   (2006.01)
*C08B 37/12*   (2006.01)
*C08B 37/02*   (2006.01)

(52) U.S. Cl.
USPC ........................... 521/32; 536/123.1; 536/112

(58) Field of Classification Search
USPC .................................. 521/32; 536/123.1, 112
See application file for complete search history.

(56) References Cited

U.S. PATENT DOCUMENTS

| 5,453,186 A | 9/1995 | Muller et al. |
| 6,783,937 B1 * | 8/2004 | Hou et al. ..................... 435/6.12 |
| 2004/0203149 A1 | 10/2004 | Childs et al. |

FOREIGN PATENT DOCUMENTS

| EP | 0 337 144 A1 | 10/1989 |
| EP | 1 473 075 A2 | 11/2004 |
| EP | 1473075 A2 * | 11/2004 |

OTHER PUBLICATIONS

International Search Report of PCT/EP2009/004952 (Aug. 24, 2009).
J. Kobayashi et al., "Aqueous Chromatography Utilizing Hydrophobicity-Modified Anionic Temperature-Responsive Hydrogel for Stationary Phases," Journal of Chromatography A, vol. 958 (2002) pp. 109-119.
W. Muller et al., "New Ion Exchangers for the Chromatography of Biopolymers," Journal of Chromatography, vol. 510 (1990) pp. 133-140.

* cited by examiner

*Primary Examiner* — Michael Bernshteyn
(74) *Attorney, Agent, or Firm* — Millen, White, Zelano & Branigan, P.C.

(57) ABSTRACT

The invention relates to a modified separating material having improved properties, to the preparation thereof, and to the use thereof for the separation of charged biopolymers from liquids.

22 Claims, No Drawings

GRAFT COPOLYMERS FOR ION EXCHANGE CHROMATOGRAPHY

The invention relates to a modified separating material, to the preparation thereof, and to the use thereof for the separation of charged biopolymers from liquids.

PRIOR ART

Ion exchange chromatography is probably the most frequently employed method for the purification of pharmaceutical proteins, peptides and other biopolymers. Virtually all industrial purification processes include one or more ion exchange steps. Of particular interest are ion exchanger resins which have a high binding capacity for the target molecules.

The use of suitable separating materials in which the ionic groups are localised exclusively on linear graft polymers, which are in turn covalently bonded to a support surface, is particularly advantageous (W. Müller, *J. Chromatography* 1990, 510, 133-140).

Functionalised polymers which are obtained by grafting corresponding functionalised monomers onto a multiplicity of different surfaces have been known for many years. If the functionalisation involves chemically bonded ionic groups, corresponding materials can be used for ion exchange chromatography.

A relatively large number of possible graft polymer structures which are intended for the fractionation of biopolymers is found in the patents EP 0 337 144 or U.S. Pat. No. 5,453,186. Graft polymers comprising more than one monomer unit (copolymerisation) are also claimed in the patents. For this graft copolymerisation, the monomers must, in order to obtain suitable exchangers, be selected in such a way that both monomers either contain basic or acidic groups or one monomer is neutral. The combination and type of monomers that are preferred for the graft copolymerisation is not explained, meaning that the person skilled in the art has to carry out a large number of experiments before he obtains separating materials which are suitable for the purification of pharmaceutical proteins, peptides and other biopolymers.

EP 1 473 075 A describes materials for ion exchanger chromatography. For the preparation of the materials, a polymer solution consisting of 2-acrylamido-2-methyl-1-propanesulfonic acid, N(isobutoxymethyl)acrylamide and hydroxymethyl methacrylate is adsorbed onto hydroxyl-containing supports, such as, for example, porous cellulose nitrate. However, this "adsorption" does not involve chemical linking between the support material and the applied coating. In the adsorption, a hydrogel, which is a water-swollen, cross-linked polymer, is polymerised in the pores of the support. It is only through the polymerisation in the pores that the material becomes sufficiently dimensionally stable so that it is pressure-stable in the application. At least three monomers are necessary for the preparation of the hydrogel used; and at least five components, namely support, monomer 1, monomer 2 and cross-linking agent and dextran, are necessary for the preparation of the actual separating material.

Kobayashi et al. [Journal of Chromatography, Vol. 958, No. 1-2, 109-119, (2002)] in turn describe a chromatography material which is obtained by grafting a polymer comprising isopropylacrylamide and acrylic acid onto silica, or silica gel. The aim of this grafting is to produce hydrophobic properties by the introduction of an uncharged monomer. Binding of the polymers to the inorganic silica is made more difficult by the fact that no aliphatic hydroxyl groups are present on the support surface and silica is stable to hydrolysis.

US 2004/203149 A1 describes chromatographic material which consists of a support material and a gel. Support-supported porous, crosslinked gels are obtained. As also described in EP 1 473 075 A, a hydrogel is polymerised in the pores of the support, giving a sufficiently dimensionally stable material which is pressure-stable in the application. Covalent bonding to the support does not occur, but instead the hydrogel is intertwined with the support. Hydrophobic support materials are preferably used. As also described by Kobayashi, the preparation of the desired separating material in all cases requires a crosslinking agent, which has a considerable influence on the binding behaviour in the application of the materials. In addition, the acrylamide preferably used is not sufficiently stable to hydrolysis.

OBJECT

The object of the present invention is therefore to prepare a support material having ionic groups which binds proteins and other biopolymers with high capacity and which can be employed for preparative applications on an industrial scale.

This support material should be stable to hydrolysis, in particular stable to alkali, in order to enable purification or regeneration of the separating material at pH≥13, with essential properties of the support being retained.

Subject-Matter of the Invention

The invention relates to separating materials comprising inorganic or organic support materials, characterised in that polymers built up from at least two monomer units are bound to the support material, where at least 2 different recurring units occur in the separating material, while one of these units carries a charge and at least one of these units carries a neutral group.

Experiments have shown that support materials derivatised with N-alkoxyalkylacrylamides as neutral comonomer are suitable as separating materials for separating off charged biomolecules, in particular charged biopolymers. Due to the graft copolymerisation with N-alkoxyalkylacrylamides, good utilisation of low charge densities on the surface is achieved.

The present object is therefore also achieved by the preparation of corresponding graft copolymers on hydroxyl-containing surfaces of porous particles or other mouldings. The graft polymers bound to these surfaces by the reaction are, in accordance with the invention, built up from two or more recurring units, where at least one of these units carries a charge and at least one unit is linked to a neutral group, so that these graft polymers are capable of binding a charged substance by ionic interaction.

The present invention therefore furthermore relates to separating materials which are capable of binding charged substances, in particular biopolymers, by ionic interaction. For the preparation of these support materials, graft polymers built up from two or more recurring monomer units, where at least one of these units carries a charge and at least one of these units is linked to a neutral group, can be bound to hydroxyl-containing surfaces of porous particles or other mouldings by chemical reaction.

The present invention relates, in particular, to corresponding separating materials which have a crosslinked synthetic polymer or a crosslinked agarose or a dextran or a composite material comprising an inorganic support with an organic coating as base support.

Separating materials of this type for ion exchange chromatography based on corresponding hydroxyl-containing base supports to the surfaces of which copolymers are covalently bonded are distinguished by the fact that
a) the base support contains aliphatic hydroxyl groups,
b) the copolymers are covalently bonded to the support,
c) the copolymers contain at least two different monomer units
d) the monomer units are linked in a linear manner,
e) the copolymer has at least one monomer unit which carries a charge in the form of a sulfonic acid or carboxylic acid or in the form of an amine or ammonium group and in addition contains and alkyl and/or alkylene groups and optionally amide groups, but no aryl groups,
or
which carries a negative charge in the form of a sulfonic acid or carboxylic acid or in the form of an amine or ammonium group and in addition contains alkyl and/or alkylene groups, but no aryl groups,
f) the copolymer has at least one uncharged monomer unit of the general formula (1)

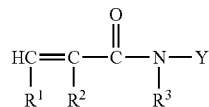
(1)

in which
$R^1$ denotes hydrogen,
$R^2$ denotes hydrogen or methyl, and
$R^3$ and Y, independently of one another, denote hydrogen, straight-chain alkyl having up to 4 C atoms, methoxypropyl, ethoxyethyl or methoxyethyl,
g) only monomer units of the same charge are combined if more than one monomer having a charge is present,
h) the ratio of the monomer units having a charge to the monomer units without a charge is in a range between 1:99 to 90:10.

The present invention preferably also relates to corresponding separating materials for ion exchange chromatography based on hydroxyl-containing base supports to the surfaces of which copolymers are covalently bonded, and which are characterised in that
a) the base support contains aliphatic hydroxyl groups,
b) the copolymers are covalently bonded to the support,
c) the copolymers contain at least two different monomer units
d) the monomer units are linked in a linear manner,
e) the copolymer has at least one monomer unit having a charge of the general formula (1), in which
$R^1$ denotes hydrogen,
Y denotes hydrogen and
$R^3$ denotes $R^4$—$SO_3M$, $R^4$—$COO$, $R^4$—$NR^9R^{10}$ or $R^4$—$NR^9R^{10}R^{11}X$
where
$R^4$ denotes straight-chain or branched alkylene having 2 to 4 C atoms,
$R^9$, $R^{10}$ and $R^{11}$, independently of one another, denote hydrogen, methyl, ethyl, propyl, phenyl or benzyl,
M denotes hydrogen, Na, K or $NH_4$ and
X denotes Cl, Br, I, or methylsulfate
or the copolymer has at least one monomer unit of the general formula (2)

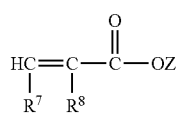
(2)

in which
$R^7$ denotes hydrogen,
$R^8$ denotes methyl,
Z denotes hydrogen, Na, K, or $NH_4$.

Preference is given to separating materials according to the invention characterised in that
f) the bound copolymer has at least one uncharged monomer unit of the general formula (1)

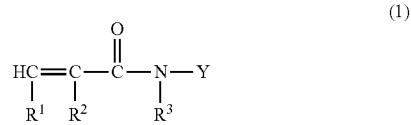
(1)

in which
$R^1$ denotes hydrogen,
$R^2$ denotes hydrogen or methyl and
$R^3$ denotes methyl, ethyl, propyl, methoxypropyl, methoxyethyl where
Y denotes hydrogen or
$R^3$ denotes methyl or ethyl where
Y denotes methyl.

A particularly preferred variant of the separating materials according to the invention is distinguished by the fact that
c) the copolymers are built up from at least two different monomer units,
e) the copolymer has at least one monomer unit having a negative charge, selected from the group 2-acrylamido-2-methylpropanesulfonic acid, 2-acrylamidoethanesulfonic acid, carboxymethylacrylamide; carboxyethylacrylamide, carboxypropylacrylamide, carboxymethlymethacrylamide, carboxyethlymethacrylamide, carboxypropylmethacrylamide, acrylic acid and methacrylic acid,
and
f) the copolymer contains at least one uncharged monomer unit selected from the group dimethylacrylamide, ethoxyethylacrylamide, methoxyethylacrylamide and methoxypropylacrylamide.

A further preferred embodiment of the separating materials described in accordance with the invention is distinguished by the fact that
c) the copolymers contain at least two different monomer units,
e) the copolymers have at least one monomer unit having a positive charge, selected from the group 2-(acryloylaminoethyl)trimethylammonium chloride, 3-(acryloylaminopropyl)trimethylammonium chloride, 2-(diethylaminoethyl)acrylamide, 2-(diethylaminoethyl)methacrylamide, 2-(dimethylaminoethyl)acrylamide, 2-(dimethylaminoethyl)methacrylamide, 3-(diethylaminopropyl)acrylamide, 3-(diethylaminopropyl)methacrylamide, 3-(diethylaminopropyl)acrylamide, 3-(diethylaminopropyl)methacrylamide, 2-(methacryloylaminoethyl)trimethylammonium chloride and 3-(acryloyl-aminopropyl)trimethylammonium chloride
and
f) the copolymers contain at least one uncharged monomer unit selected from the group dimethylacrylamide, ethoxyethylacrylamide, methoxyethylacrylamide and methoxypropylacrylamide.

The present invention additionally relates to a process for the preparation of separating materials according to the invention, preferably of graft copolymers on hydroxyl-containing surfaces of porous particles or other mouldings, which is characterised in that graft polymers built up from two or more recurring monomer units, where at least one of these units carries a charge and at least one of these units carries an uncharged group which are bound to a hydroxyl-containing surface by chemical reaction, giving materials which are capable of binding charged substances, in particular biopolymers, by ionic interaction.

DETAILED DESCRIPTION OF THE INVENTION

The use of flexible graft polymers ("tentacles") bound to the support surface as ion-exchanging group is known. Thus, the graft polymer in the commercially available cation exchanger Fractogel® EMD $SO_3^-$ (M) is built up only from one recurring unit having sulfonic acid groups.

The patents EP 0 337 144 or U.S. Pat. No. 5,453,186 give no information on monomer combinations which are to be preferred in the synthesis of an ion exchanger. The examples also only describe graft polymerisations with one monomer which result directly in an ion exchanger.

In particular, the grafting of functionalised acrylamides and acrylic acid has been investigated, since the polymers formed therefrom are stable to hydrolysis under alkaline conditions. In addition, the poly(acrylamides) are able to form hydrogen bonds, which is a major advantage for use owing to the better swellability in aqueous solutions and thus their hydrophilicity.

For the preparation of the separating materials according to the invention, hydrophilic chromatography supports, such as, for example, Fractogel TSK HW65 (M) or the commercially available Toyopearl HW-65 (S), can be used. These supports are modified with graft copolymers.

For the preparation of the materials according to the invention, other chromatography supports can also be used. However, it is preferred for the material used to have reactive groups, preferably OH groups, which are accessible to the graft polymerisation reaction. Suitable support materials can therefore also consist, for example, of organic polymers. Such organic polymers can be polysaccharides, such as agarose, dextrans, starch, cellulose, etc., or synthetic polymers, such as poly(acrylamides), poly(methacrylamides), poly(acrylates), poly(methacrylates), hydrophilically substituted poly(alkyl allyl ethers), hydrophilically substituted poly(alkyl vinyl ethers), poly(vinyl alcohols), poly(n-vinylureas), poly(N-vinylpyrrolidones), poly(styrenes) and copolymers of the corresponding monomers. These organic polymers can preferably also be employed in the form of a crosslinked hydrophilic network. These crosslinked hydrophilic polymers also include those comprising styrene and divinylbenzene, which can preferably be employed, like other hydrophobic polymers, in a hydrophilised form.

Alternatively, inorganic materials, such as silica, zirconium oxide, titanium dioxide, aluminium oxide, etc., can be employed as supports. Equally, composite materials can be employed as suitable support materials, i.e., for example, separating materials according to the invention can be obtained by derivatisations of the surface, for example, of inorganic particles or mouldings which are derivatised in the manner according to the invention. An example thereof are particles which can themselves be magnetised by copolymerisation of magnetisable particles or of a magnetisable core.

However, preference is given to the use of hydrophilic support materials which are stable to hydrolysis or can only be hydrolysed with difficulty since the materials according to the invention must withstand alkaline purification or regeneration at pH≥13 over an extended use duration. The supports may already carry low-molecular-weight ligands. Ligands may carry one or more charged groups, hydrophobic groups or groups which are able to form hydrogen bonds. Preference is given to ligands which carry the same charge as the graft polymer.

The support materials may also consist of irregularly shaped or spherical particles, whose particle size can be between 2 and 1000 μm. Preference is given to particle sizes between 3 and 300 μm.

The support materials may, in particular, be in the form of non-porous or preferably porous particles. The pore sizes can be between 2 and 300 nm. Preference is given to pore sizes between 5 and 200 nm.

Equally, the support materials may also be in the form of membranes, fibres, hollow fibres, coatings or monolithic mouldings. Monolithic mouldings are three-dimensional bodies, for example in cylindrical form.

For the preferred graft polymerisation, at least one positively or negatively charged monomer is used. If a plurality of charged monomers are employed, only monomers having the same charge can be mixed in order to obtain separating materials having properties which are improved in accordance with the invention. Monomers having a negative group can have, for example, sulfonic acid or carboxyl groups.

Suitable monomers having sulfonic acid groups are, for example, acrylates of the formula (2) where $Z=R^4—SO_3M$, in which $R^7$ and $R^8$, independently of one another, can have the meanings hydrogen or alkyl having up to 6 C atoms, preferably hydrogen or methyl, carboxyl or carboxymethyl, and in which $R^4$ can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene.

M is a hydrogen atom or a metal cation, such as sodium or potassium, or an ammonium cation. M is selected in such a way that the monomer is water-soluble.

Mention is made by way of example of the sulfoalkyl acrylates, such as 3-sulfopropyl acrylate or 2-sulfoethyl acrylate, and the sulfoalkyl methacrylates, such as 3-sulfopropyl methacrylate or 2-sulfoethyl methacrylate.

Preference is given to the use of the acrylamides of the general formula (1)

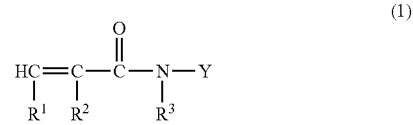

where $R^3=R^4—SO_3M$, in which $R^1$, $R^2$ and Y, independently of one another, can have the meanings hydrogen or alkyl having up to 6 C atoms, can preferably be hydrogen or methyl. $R^1$ and $R^2$ can likewise be, independently of one another, carboxyl or carboxymethyl.

$R^3$ can also be $R^4—SO_3M$, and in which $R^4$ can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene.

M is a hydrogen atom or a metal cation, such as sodium or potassium, or an ammonium cation. M is selected in such a way that the monomer is water-soluble.

Suitable acrylamides which may be mentioned here by way of example are 2-acrylamido-2-methylpropanesulfonic acid (AMPS) and 2-acrylamidoethanesulfonic acid.

Suitable monomers having a carboxyl group can also be, for example, acrylates of the general formula (2)

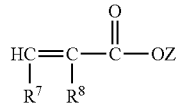

(2)

where $Z=R^5$—COOM, in which $R^1$ and $R^2$, independently of one another, can have the meanings hydrogen or alkyl having up to 6 C atoms, preferably hydrogen or methyl, carboxyl or carboxymethyl, and in which $R^5$ can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene. M is a hydrogen atom or a metal cation, such as sodium or potassium, or an ammonium cation. M is selected in such a way that the monomer is water-soluble.

Mention is made by way of example of the carboxyalkyl acrylates, such as carboxyethyl acrylate, and the carboxyalkyl methacrylates. Preference is given to the use of the acrylamides of the formula (1) where $R^3=R^5$—COOM, in which $R^1$, $R^2$ and Y, independently of one another, have the meanings hydrogen or alkyl having up to 6 C atoms, preferably hydrogen or methyl, $R^1$ and $R^2$ can likewise be, independently of one another, carboxyl or carboxymethyl.

$R^3$ can also be $R^5$—COOM, and in which $R^5$ can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene.

M is a hydrogen atom or a metal cation, such as sodium or potassium, or an ammonium cation. M is selected in such a way that the monomer is water-soluble.

Particular preference is given to the use of unsaturated carboxylic acids of the general formula (2) where Z=M, in which $R^7$ and $R^8$, independently of one another, can have the meanings hydrogen or alkyl having up to 6 C atoms, preferably hydrogen or methyl, carboxyl or carboxymethyl. M is a hydrogen atom or a metal cation, such as sodium or potassium, or an ammonium cation. M is selected in such a way that the monomer is water-soluble. Mention may be made by way of example of maleic acid, itaconic acid, citraconic acid, mesaconic acid, or fumaric acid. Of these, particular preference is given to monomers of the formula (2) where Z=M, in which $R^7$ denotes hydrogen and R8 denotes hydrogen or alkyl having up to 3 C atoms. For this purpose, mention may be made by way of example of acrylic acid and methacrylic acid.

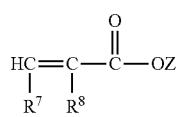

(2)

Monomers having a positive group can carry, for example, primary, secondary or tertiary amino groups or can be quaternary ammonium salts. Suitable monomers having amino groups are, for example, acrylates of the formula (2) where $Z=R^4$—$NR^9R^{10}$, in which $R^7$ and $R^8$, independently of one another, can have the meanings hydrogen or alkyl having up to 6 C atoms, preferably hydrogen or methyl, and in which $R^4$ can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene, and in which $R^9$ and $R^{10}$, independently of one another, have the meanings hydrogen, alkyl, phenyl or alkylphenyl, such as, for example, methyl, ethyl or benzyl. Mention is made by way of example of the aminoalkyl acrylates, such as 2-(diethylaminoethyl)acrylate, 2-(dimethylaminoethyl)acrylate or 2-(dimethylaminopropyl)acrylate, and the aminoalkyl methacrylates, such as 2-(diethylaminoethyl)methacrylate, 2-(dimethylaminoethyl)methacrylate or 3-(diethylaminopropyl)methacrylate.

Preference is given to the use of the acrylamides of the formula (1) where $R^3=R^4$—$R^4$—$NR^9R^{10}$, in which $R^1$, $R^2$ and Y, independently of one another, have the meanings hydrogen or alkyl having up to 6 C atoms, preferably hydrogen or methyl, and in which R4 can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene, and in which $R^9$ and $R^{10}$, independently of one another, have the meanings hydrogen, alkyl, phenyl or alkylphenyl, such as, for example, methyl, ethyl or benzyl. Suitable acrylamides which may be mentioned here by way of example are 2-(diethylaminoethyl)-acrylamide, 2-(dimethylaminoethyl)acrylamide, 3-(diethylaminopropyl) acrylamide or 3-(diethylaminopropyl)acrylamide, and suitable methacrylamides which may be mentioned here by way of example are 2-(diethylaminoethyl)-methacrylamide, 2-(dimethylaminoethyl)methacrylamide, 3-(diethylaminopropyl)methacrylamide or 3-(diethylaminopropyl)methacrylamide.

Suitable monomers which are quaternary ammonium salts are, for example, acrylates of the general formula (2) in which Z has the meaning $R^4$—$NR^9R^{10}R^{11}X$ and in which $R^7$ and $R^8$, independently of one another, can have the meanings hydrogen or alkyl having up to 6 C atoms, preferably hydrogen or methyl, and in which R4 can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene, and in which $R^9$, $R^{10}$ and $R^{11}$, independently of one another, have the meanings hydrogen, alkyl, phenyl or alkylphenyl, such as, for example, methyl, ethyl or benzyl. X is an anion and is selected in such a way that the monomer is water-soluble, and can be, for example, chloride, bromide, iodide or methylsulfate. Mention is made by way of example of the acryloxyalkylammonium salts, such as [2-(acryloxy)ethyl-]trimethylammonium chloride, and methacryloxyalkylammonium salts, such as [2-(methacryloxy)ethyl]trimethylammonium chloride.

Preference is given to the use of the acrylamides of the general formula (1) where $R^3=R^4$—$NR^9R^{10}R^{11}X$, in which $R^1$, $R^2$ and Y, independently of one another, have the meanings hydrogen or alkyl having up to 6 C atoms, preferably hydrogen or methyl, and in which $R^4$ can be a straight-chain alkylene group having 1 to 8 C atoms, such as, for example, methylene, ethylene, propylene or hexylene, or a branched alkylene group having 1 to 8 C atoms, such as, for example, isopropylenes or isobutylene, and in which $R^9$, $R^{10}$ and $R^{11}$, independently of one another, have the meanings hydrogen, alkyl, phenyl or alkylphenyl, such as, for example, methyl, ethyl or benzyl. X is an anion and is selected in such a way that the monomer is water-soluble, and can be, for example, chloride, bromide, iodide or methylsulfate. Suitable acrylamides which may be mentioned here by way of example are 2-(acryloylaminoethyl)trimethylammonium chloride and 3-(acryloylaminopropyl)trimethylammonium chloride. Suitable methacrylamides which may be mentioned here by way of example are 2-(methacryloylaminoethyl)trimethylammonium chloride and 3-(acryloylaminopropyl)trimethylammonium chloride.

As further component, at least one uncharged monomer, which is preferably hydrophilic, is required. Neutral monomers which are suitable for this purpose are, for example, lower alkyl acrylates, such as methyl acrylate, lower alkyl methacrylates, such as methyl methacrylate. Preference is given to the use of acrylamides of the general formula 1 where $Y=R^6$, in which $R^1$ and $R^2$, independently of one another, are hydrogen or methyl and in which $R^3$ and $R^6$, independently of one another, denote hydrogen or alkyl having up to 4 C atoms. $R^3$ and/or $R^6$ thus denote hydrogen or lower alkyl. The latter here preferably has the meaning methyl, ethyl, butyl, isopropyl, 3-butyl or isobutyl, and in addition the meaning of alkoxyalkyl having up to 4 C atoms, such as, for example, methoxyethyl or ethoxyethyl. Mention may be made here by way of example of acrylamide (AAm), dimethylacrylamide, ethoxyethylacrylamide, methacrylamide, methoxyethylacrylamide and methoxypropylacrylamide. Preference is given to the N-substituted amides, since they are more stable to hydrolysis than esters and unsubstituted amides.

The actual polymer can be prepared in various ways. In the case of "grafting onto", polymer chains must firstly be formed from the monomers and bound to the surface in a second step. In the case of "grafting from", a polymerisation reaction is initiated on the surface, and the graft polymer is built up directly from individual monomers. Other polymerisation methods which allow binding to the surface of the support material can also be employed.

Preference is given to the second method and particular preference is given to variants in which only a few by-products, such as a non-covalently bonded polymer, which have to be separated off are formed. Processes with controlled free-radical polymerisation, such as, for example, the method of atom-transfer free-radical polymerisation (ATRP), appear particularly interesting. Here, an initiator group is covalently bonded to the support surface in the desired density in a first step. An initiator group can be, for example, a halide bonded via an ester function, as in a 2-bromo-2-methylpropionic acid ester. The graft polymerisation is carried out in a second step in the presence of copper(I) salts. A preferred one-step graft polymerisation reaction can be initiated by cerium(IV) on the hydroxyl-containing support, without the support having to be activated. This reaction is normally carried out in dilute mineral acids. In order to carry out this graft polymerisation, the acid is usually employed in an aqueous solution with a concentration in the range from 1 to 0.00001 mol/l, preferably from 0.1 to 0.001. Very particular preference is given to the use of dilute nitric acid, which is employed with a concentration in the range from 0.1 to 0.001 mol/l.

For experimental series on grafting, preference has been given to the use of functionalised acrylamides and acrylic acid, since the polymers formed therefrom are stable to hydrolysis under alkaline conditions. It has been found that separating materials derivatised by graft polymerisation which have properties which are improved in accordance with the invention are obtained if suitable support materials are graft-polymerised with the monomers mentioned in the following table.

2-acrylamido-2-methylpropanesulfonic acid (AMPS)
2-acrylamidoethanesulfonic acid
acrylic acid
2-(acryloylaminoethyl)trimethylammonium chloride
2-(diethylaminoethyl)acrylamide
dimethylacrylamide
methoxyethylacrylamide By way of example, the following support-bound graft copolymers are prepared on suitable supports, such as, for example, Fractogel TSK HW65 (M) or (S), by combination of two monomers and investigated with respect to their properties as cation exchanger, in particular their binding capacity:
poly(AMPS, dimethylacrylamide),
poly(AMPS, methoxyethylacrylamide)

In order to obtain graft polymers having advantageous properties, charged monomers and uncharged monomers are preferably mixed in such a ratio to one another that the proportion of the charged components is 1-90 mol % relative to the total amount of monomers, preference is given to a proportion in the range 3-70 mol %, based on the total amount of monomers. For the preparation of the separating materials according to the invention, the monomers are normally added in excess to the support material. 0.05 to 100 mol of total monomer are employed per litre of sedimented polymer material, preferably 0.05-25 mol/l are employed.

It has been found that a charged and an uncharged acrylamide can be graft-polymerised as a mixture and that the incorporation ratios corresponding to the monomer concentrations employed are obtained (Table 1).

The graft polymers prepared in accordance with the invention from the charged monomers and uncharged are more or less in strongly ionised form in the aqueous medium corresponding to the pH values of the respective ionisable groups present therein and depending on the current pH of the aqueous environment, in the form of carboxylate or sulfonate groups or protonated secondary or tertiary amino groups or quaternary ammonium groups. The materials according to the invention are therefore particularly suitable for use in ion exchange chromatography. The uncharged monomer units ensure that the average separation between two charges on a graft polymer is greater than in a graft polymer which consists only of one charged monomer unit. Since the graft polymers are all linked to a surface, they form a hydrogel thereon, which correspondingly has a lower charge density, due to the presence of neutral groups, than a hydrogel which consists only of one charged monomer unit.

For the assessment of the cation exchangers, firstly the static binding capacity of lysozyme and polyclonal human IgG (Gammanorm) is investigated in the range pH 5-7. The binding capacity is determined after elution of the protein by increasing the salt concentration to about 1 M NaCl.

The dynamic binding capacity is measured at various flow rates, so that the cation exchangers packed into columns is charged with protein at contact times of 2 or 8 min. To this end, charging is carried out to a breakthrough of 10% with IgG (Gammanorm) dissolved in a buffer comprising 25 mM sodium phosphate and 25 mM sodium acetate at pH 5.0. The elution is carried out by increasing the salt concentration to about 1 M NaCl at the pH of the binding buffer. The binding capacity is calculated from the protein concentration (280 nM) in the eluate. The results of corresponding experiments are shown in Table 2.

Surprisingly, it has been found that comparable static binding capacities can be achieved, although less charged monomer is provided for the graft polymerisation. Thus, the product called 08PP063 comprising AMPS and dimethylacrylamide even has a higher static binding capacity for lysozyme and IgG compared with the product 07PP221, although only 66% of the amount of AMPS used for 07PP221 was employed for 08PP063.

Surprisingly, it has, in addition, been found that the separating materials according to the invention comprising graft copolymers achieve significantly higher dynamic binding capacities than comparative gels. This applies, in particular, to the binding of large molecules, such as IgG, and at high flow rates (short contact times) during the charging. For example, the graft copolymer 07SW261 comprising AMPS and methoxyethylacrylamide, in which the molar ratio of charged to neutral monomer units is about 1:0.9 (see examples), achieves a 30% higher binding capacity at pH 5.0 and a contact time of 2 min than the commercially available Fractogel® EMD SO$_3$M.

The novel arrangement of the negative charges in the space above the support surface enables, in particular, relatively large charged molecules to diffuse into the hydrogel more easily. Thus, the IgG carries more positive than negative charges (pH<pI) at pH 5.0, at which the binding was investigated. Possibly, fewer repulsive interactions of the graft polymers with the negative charges on the IgG arise. Grafting according to the invention on porous supports thus enables large molecules to be transported more quickly from the outer surface of the support into the inner pore system and nevertheless to be bound sufficiently strongly for ion exchange chromatography.

The materials according to the invention can also be described as polymers provided with separation effectors. They can be used for the selective, partially selective or non-selective binding or adsorption of one or more target components with the aim of separation out of a matrix, or for the selective, partially selective or non-selective binding or adsorption of one or more secondary components with the aim of separation of the secondary component out of a matrix, but also for the separation of a substance mixture without binding or adsorption of one or more components merely on the basis of the molecular size by size exclusion chromatography, the isolation, enrichment and/or depletion of biopolymers from natural sources, the isolation, enrichment and/or depletion of biopolymers from recombinant sources, the isolation, enrichment and/or depletion of bioploymers from immortalised cell lines and culture supernatants thereof, the isolation, enrichment and/or depletion of biopolymers from B-cell lines and derivatives thereof, lymph cells and hybridoma cell lines and culture supernatants thereof, the isolation, enrichment and/or depletion of proteins and peptides, the isolation, enrichment and/or depletion of enzymes, the isolation, enrichment and/or depletion of monoclonal and polyclonal antibodies and naturally occurring or recombinant antibody fragments, the isolation, enrichment and/or depletion of phosphorylated peptides/proteins and nucleic acids, the isolation, enrichment and/or depletion of food additives, the isolation, enrichment and/or depletion of mono- and polysaccharides, the isolation, enrichment and/or depletion of glycosylated proteins, the isolation, enrichment and/or depletion of single-stranded or double-stranded DNA, the isolation, enrichment and/or depletion of plasmid DNA, the isolation, enrichment and/or depletion of RNA, the isolation, enrichment and/or depletion of viruses, the isolation, enrichment and/or depletion of host cell proteins, the isolation, enrichment and/or depletion of oligo- and polynucleotides, the isolation, enrichment and/or depletion of liposomes, the isolation, enrichment and/or depletion of products from blood and milk, the isolation, enrichment and/or depletion of low-molecular-weight medicament active compounds (APIs: active pharmaceutical ingredient), the separation of an API from an API medicament carrier (for example an API/liposome adduct or an API/nanoparticle adduct), the isolation, enrichment and/or depletion of enantiomers The biopolymers originate predominantly, but not exclusively, from liquid sources or are present therein, such as, for example, in body fluids, such as blood, sera, saliva or urine, organ extracts, milk, whey, plant extracts, cell extracts, cell cultures, fermentation broths, animal extracts. Antibodies can originate, for example, from mammal cells of rodents or hybridoma cells.

The target molecules are separated from at least one or more other substances from a sample, where the sample which comprises the target molecule is dissolved in a liquid, which is brought into contact with the material according to the invention. Contact times are usually in the range from 30 seconds to 24 hours. It is advantageous to work in accordance with the principles of liquid chromatography by passing the liquid through a chromatography column which contains the separating material according to the invention. The liquid can run through the column merely through its gravitational force or be pumped through by means of a pump. An alternative method is batch chromatography, in which the separating material is mixed with the liquid by stirring or shaking for as long as the target molecules or biopolymers need to be able to bind to the separating material. It is likewise possible to work in accordance with the principles of the chromatographic fluidised bed by introducing the liquid to be separated into, for example, a suspension comprising the separating material, where the separating material is selected so that it is suitable for the desired separation owing to its high density and/or a magnetic core.

The target molecule usually binds to the material according to the invention. The separating material can subsequently be washed with a wash buffer, which preferably has the same ion strength and the same pH as the liquid in which the target molecule is brought into contact with the separating material. The wash buffer removes all substances which do not bind to the separating material. Further washing steps with other suitable buffers may follow without desorbing the target molecule. The desorption of the bound target molecule is carried out by increasing the ion strength in the eluent or by changing the pH in the eluent. The target molecule can thus be obtained in a purified and concentrated form in the eluent. The target molecule usually has a purity of 70% to 99%, preferably 85% to 99%, particularly preferably 90%-99%, after desorption.

However, it is also possible for the target molecule to remain in the liquid, but for other accompanying substances to bind to the separating material. The target molecule is then obtained directly by collecting the column eluate in through-flow. It is known to the person skilled in the art how he has to adapt the conditions, in particular the pH and/or the conductivity, in order to bind a specific biopolymer to a separating material, or whether it is advantageous for the purification task not to bind the target molecule.

The separating material according to the invention can be used in a first chromatographic purification step (capture step) of a work-up process for a biopolymer. If the capture step is carried out with other separating materials, it can be employed in one of the chromatographic purification steps which follow the capture step in order to remove the residual impurities.

The present description enables the person skilled in the art to apply the invention comprehensively. Even without further comments, it is therefore assumed that a person skilled in the art will be able to utilise the above description in the broadest scope.

If anything is unclear, it goes without saying that the publications and patent literature cited should be consulted. Accordingly, these documents are regarded as part of the disclosure content of the present description.

For better understanding and in order to illustrate the invention, examples are given below which are within the scope of protection of the present invention. These examples also serve to illustrate possible variants.

Furthermore, it goes without saying to the person skilled in the art that, both in the examples given and also in the remainder of the description, the component amounts present in the compositions always only add up to 100% by weight or mol %, based on the composition as a whole, and cannot exceed this, even if higher values could arise from the percent ranges indicated. Unless indicated otherwise, % data are therefore % by weight or mol %, with the exception of ratios, which are shown in volume data.

The temperatures given in the examples and the description as well as in the claims are always in ° C.

EXAMPLES

Procedure for the preparation of a graft copolymer comprising 2-acrylamido-2-methylpropanesulfonic acid and 2-methoxyethylacrylamide (batch 07SW261)

4.2 g of methoxyethylamine in 30 ml of deionised water is cooled to 0-5° C. in a glass reaction apparatus with a paddle stirrer. 6.6 g of 32% sodium hydroxide solution is metered in via a dropping funnel and 4.8 g of acryloyl chloride is metered in from a second dropping funnel with vigorous stirring at an internal temperature of 0-5° C. When the addition is complete, the solution is stirred at 5° C. for a further 30 min and adjusted to pH 6 using 65% nitric acid and made up to a total volume of 180 ml with deionised water.

A suspension is prepared from this solution, 78 g of filter-moist Fractogel TSK HW65 (M) (washed with dilute mineral acid and deionised water) and a solution of 16.4 g of 2-acrylamido-2-methylpropanesulfonic acid (AMPS) and 9.9 g of 32% sodium hydroxide solution in 30 ml of deionised water. The pH is adjusted to 6 using 32% sodium hydroxide solution and 65% nitric acid.

An initiator solution comprising 1.6 g of ammonium cerium(IV) nitrate and 0.4 g of 65% nitric acid in 40 ml of deionised water is initially introduced in a dropping funnel with pressure equalisation. The entire apparatus is rendered inert by repeated (3×) evacuation and decompression with nitrogen. The suspension is subsequently warmed to 40° C. in the apparatus.

The initiator solution is added to the inertised suspension at an internal temperature of 40° C. with stirring. Under a gentle stream of nitrogen, the suspension is stirred at 40° C. for 18 hours. The reaction solution is then filtered off with suction through a glass filter frit (P2), and the gel is washed on the frit with in each case 100 ml of wash solution as follows:
3× deionised water
8×1M sulfuric acid, 0.2M ascorbic acid
3× deionised water
2×1M NaOH
3× deionised water The gel is suspended in 200 ml of deionised water and adjusted to pH 7 using 25% hydrochloric acid. The storage is carried out in 20% ethanol at room temperature.

Preparation of a graft copolymer comprising 2-acrylamido-2-methylpropanesulfonic acid and dimethylacrylamide (batch 07PP221)

A suspension is prepared from 78 g of filter-moist Fractogel TSK HW65 (M) (washed with dilute mineral acid and deionised water) and a solution of 5.1 g of dimethylacrylamide, 16.7 g of 2-acrylamido-2-methylpropanesulfonic acid and 10.4 g of 32% sodium hydroxide solution in 97 ml of deionised water in a glass reaction apparatus with a paddle stirrer. The pH is adjusted to 6 using 32% sodium hydroxide solution and 65% nitric acid, and the mixture is made up to a total volume of 200 ml with deionised water.

An initiator solution comprising 1.6 g of ammonium cerium(IV) nitrate and 0.4 g of 65% nitric acid in 15 ml of deionised water is initially introduced in a dropping funnel with pressure equalisation. The entire apparatus is rendered inert by repeated (3×) evacuation and decompression with nitrogen. The suspension is subsequently warmed to 40° C. in the apparatus.

The initiator solution is added to the inertised suspension at an internal temperature of 40° C. with stirring. Under a gentle stream of nitrogen, the suspension is stirred at 40° C. for 22 hours. The reaction solution is then filtered off with suction through a glass filter frit (P2), and the gel is washed on the frit with in each case 100 ml of wash solution as follows:
7× deionised water
10×1M sulfuric acid, 0.2M ascorbic acid
5× deionised water
2×1M sodium hydroxide solution
3× deionised water
1×50 mM phosphate buffer pH 7
2× deionised water The product is stored in 20% ethanol at room temperature.

Preparation of a graft copolymer comprising 2-acrylamido-2-methylpropanesulfonic acid and dimethylacrylamide (batch 08PP063)

A suspension is prepared from 100 g of filter-moist Fractogel TSK HW65 (S) (washed with dilute mineral acid and deionised water) and a solution of 8.0 g of dimethylacrylamide, 11.1 g of 2-acrylamido-2-methylpropanesulfonic acid and 6.9 g of 32% sodium hydroxide solution in 60 ml of deionised water in a glass reaction apparatus with a paddle stirrer. The pH is adjusted to 6.2 using 32% sodium hydroxide solution and 65% nitric acid, and the mixture is made up to a total volume of 190 ml with deionised water.

An initiator solution comprising 1.6 g of ammonium cerium(IV) nitrate and 0.4 g of 65% nitric acid in 25 ml of deionised water is initially introduced in a dropping funnel with pressure equalisation. The entire apparatus is rendered inert by repeated (3×) evacuation and decompression with nitrogen. The suspension is subsequently warmed to 40° C. in the apparatus.

The initiator solution is added to the inertised suspension at an internal temperature of 40° C. with stirring. Under a gentle stream of nitrogen, the suspension is stirred at 40° C. for 22 hours. The reaction solution is then filtered off with suction through a glass filter frit (P2), and the gel is washed on the frit with in each case 100 ml of wash solution as follows:
7× deionised water
10×1M sulfuric acid, 0.2M ascorbic acid
5× deionised water
2×1M sodium hydroxide solution
3× deionised water
1×50 mM phosphate buffer pH 7.0
2× deionised water
2×20% ethanol/150 mM NaCl The product is stored in 20% ethanol at room temperature. Determination of the Chemical Composition of the Graft Polymers The functional groups can be cleaved off the graft polymers, which are polyacrylamide chains, by acid hydrolysis. The functional groups are liberated as amine. Primary amines can be analysed quantitatively by HPLC after derivatisation with ortho-phthalaldehyde and mercaptoethanol. For calibration, commercial amines are used or the monomer used in the synthesis, which must then be hydrolysed like the graft polymer.

1000 µl of 5 M hydrochloric acid are added to 10 mg of dry gel, the mixture is treated in an ultrasound bath and subsequently heated at 125° C. for 10 hours in a 1 ml pressure container.

After cooling to room temperature, the pressure container is opened. About 200 µl of supernatant is pipetted off and centrifuged (8000 rpm) for 5 min.

40 µl of the clear supernatant are neutralised using 176 µl of 1 M sodium hydroxide solution, and 325 µl of 0.5 M borate buffer, pH 9.5, and 119 µl of acetonitrile/water 8:2 (V/V) are added and mixed. 100 µl of OPA reagent, which is prepared from 100 mg of ortho-phthalaldehyde, 9 ml of methanol, 1 ml of 0.5 M borate buffer pH 9.5 and 100 µl of mercaptoethanol, is added, and the mixture is shaken vigorously. After a reaction time of 2 minutes, the sample is analysed by HPLC (UV detection 330 nm).

TABLE 1

The analysis of the graft polymer of 07SW261 (calibration using AMPS and ethanolamine) compared with the amounts of monomer employed.

| Unit | Use of monomer per g of filter-moist gel | Monomer unit per g of dry grafted gel |
|---|---|---|
| AMPS | 1.0 mmol/g | 0.70 µmol/g |
| Methoxyethylacrylamide | 0.67 mmol/g* | 0.63 µmol/g |

*Use of acryloyl chloride

Determination of the Static IgG Binding Capacity (Microtitre Plate Format)

All gel suspensions are adjusted to a gel sediment volume of 50% using 20% ethanol in water. A filter plate is filled with binding buffer and with in each case 20 µl of the homogenised gel suspension. The filter plate is then sucked off in a vacuum station.

A deep-well plate is filled with binding buffer, protein stock solution (polyclonal human IgG Gammanorm, Octapharma, or lysozyme in water) is added and mixed so that the concentration is 9.3 mg of plgG per ml or 12.5 mg of lysozyme per ml.

200 µl of protein solution are added to the gel in the filter plate and shaken for 15 min in a shaker. The filter plate is sucked off in the vacuum station. Washing with 100 µl of binding buffer each time and sucking off is carried out twice. In each case 200 µl of elution buffer (20 mM phosphate, 1 M sodium chloride, pH 7) are then added to the filter plate, and shaking is carried out for 5 min. The supernatant is sucked into a UV plate in the vacuum station, and the plate is measured at 280 nm in the photometer.

The IgG binding capacities, calculated from the eluate, per ml of gel sediment volume (IgG SBC) are listed in Table 2. The binding buffers used are 25 mM sodium phosphate, 25 mM sodium acetate, pH 5 for plgG and 25 mM sodium phosphate, 25 mM sodium acetate, pH 7 for lysozyme.

Determination of the Dynamic IgG Binding Capacity

Columns having a capacity of 1 ml are packed (Proteo-Cart columns with a bed depth of 19 mm and 20% compression). The columns are charged with an IgG solution having a content of 1 g/l in buffer A (prepared from polyclonal human IgG Gammanorm, Octapharma) to a breakthrough of 10%. The flow rate is selected so that the contact time on the column is 2 or 8 min. After rinsing with buffer A, the column is eluted with buffer B.

Buffer A: 25 mM sodium phosphate, 25 mM sodium acetate, pH 5.0
Buffer B: 25 mM sodium phosphate, 25 mM sodium acetate, 1 M NaCl, pH 5.0

The dynamic binding capacity (DBC) of polyclonal human IgG is calculated from the photometrically (280 nm) determined amount of protein in the eluate and indicated per ml of packed gel (Table 2).

TABLE 2

Static and dynamic binding capacity (SBC and DBC) of polyclonal human IgG (Gammanorm) at pH 5.0 in mg of protein per ml of sedimented or packed gel.

| Batch | Lysozyme SBC | IgG SBC | IgG DBC[1] | IgG DBC[2] |
|---|---|---|---|---|
| Fractogel EMD SO3M | 104 | 124 | 70 | 131 |
| 07SW261 | 110 | 121 | 91 | 139 |
| 07PP221 | 86 | 126 | 82 | 138 |
| 08PP063 | 119 | 130 | 157 | 164 |

[1]Contact time 2 min
[2]Contact time 8 min

The invention claimed is:
1. Separating materials for ion exchange chromatography, comprising:
 a support material comprising a crosslinked synthetic polymer, a crosslinked agarose, a crosslinked dextran, or a composite material comprising an inorganic support with an organic coating, and
 copolymers covalently bonded to the surface of said support material, wherein
  a) the support material contains aliphatic hydroxyl groups,
  b) the copolymers are covalently bonded to the support material,
  c) the copolymers contain at least two different monomer units,
  d) the monomer units are linked in a linear manner,
  e) the copolymer has at least one monomer unit which carries a charge in the form of a sulfonic acid, of a carboxylic acid or in the form of an amine or ammonium group and contains alkyl and/or alkylene groups and optionally amide groups, but no aryl groups,
  f) the copolymer has at least one uncharged monomer unit of formula (1)

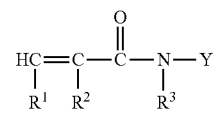

(1)

in which
R$^1$ denotes hydrogen,
R$^2$ denotes hydrogen or methyl, and
R$^3$ and Y, independently of one another, denote hydrogen, straight-chain alkyl having up to 4 C atoms, methoxypropyl, ethoxyethyl or methoxyethyl,
  g) only monomer units of the same charge are combined if more than one monomer having a charge is present, and
  h) the ratio of the monomer units having a charge to the monomer units without a charge is in a range between 1:99 to 90:10.

2. Separating materials for ion exchange chromatography according to claim 1, wherein
said at least one monomer unit which carries a charge is of the following formula

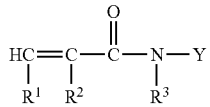

wherein
R$^1$ denotes hydrogen,
R$^2$ denotes hydrogen or methyl,
Y denotes hydrogen and
R$^3$ denotes R$^4$—SO$_3$M, R$^4$—COO, R$^4$—NR$^9$R$^{100}$r R$^4$—NR$^9$R$^{10}$R$^{11}$X,
R$^4$ denotes straight-chain or branched alkylene having 2 to 4 C atoms,
R$^9$, R$^{10}$ and R$^{11}$, independently of one another, denote hydrogen, methyl, ethyl, propyl, phenyl or benzyl,
M denotes hydrogen, Na, K or NH$_4$, and
X denotes Cl, Br, I, or methylsulfate,
or the copolymer has at least one monomer unit of formula (2)

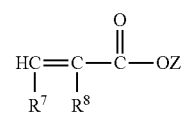 (2)

in which
R$^7$ denotes hydrogen,
R$^8$ denotes methyl,
Z denotes hydrogen, Na, K, or NH$_4$.

3. Separating materials for ion exchanger chromatography according to claim 1, wherein
in formula (1),
R$^1$ denotes hydrogen,
R$^2$ denotes hydrogen or methyl, and
R$^3$ denotes methyl, ethyl, propyl, methoxypropyl, or methoxyethyl and Y denotes hydrogen, or
R$^3$ denotes methyl or ethyl and Y denotes methyl.

4. Separating materials according to claim 1, wherein
said at least one monomer unit which carries a charge is at least one monomer unit having a negative charge selected from 2-acrylamido-2-methylpropanesulfonic acid, 2-acrylamidoethanesulfonic acid, carboxymethylacrylamide; carboxyethylacrylamide, carboxypropylacrylamide, carboxymethlymethacrylamide, carboxyethylmethacrylamide, carboxypropylmethacrylamide, acrylic acid and methacrylic acid, and
said at least one uncharged monomer unit is selected from dimethylacrylamide, ethoxyethylacrylamide, methoxyethylacrylamide and methoxypropylacrylamide.

5. Separating materials according to claim 1, wherein
said at least one monomer unit which carries a charge is at least one monomer unit having a positive charge selected from 2-(acryloylaminoethyl)trimethylammonium chloride, 3-(acryloylaminopropyl)trimethylammonium chloride, 2-(diethylaminoethyl)acrylamide, 2-(diethylaminoethyl)methacrylamide, 2-(dimethylaminoethyl)acrylamide, 2-(dimethylaminoethyl)methacrylamide, 3-(diethylaminopropyl)acrylamide, 3-(diethyl-ethyl-aminopropyl)methacrylamide, 3-(diethylaminopropyl)acrylamide, 3-(diethylaminopropyl)-methacrylamide, 2-(methacryloylaminoethyl)trimethylammonium chloride and 3-(acryloylaminopropyl)trimethylammonium chloride, and
said at least one uncharged monomer unit is selected from dimethylacrylamide, ethoxyethylacrylamide, methoxyethylacrylamide and methoxypropylacrylamide.

6. Separating materials according to claim 1, wherein the support material is hydrophilic.

7. Separating materials according to claim 1, wherein the support material contains irregularly shaped and/or spherical particles, whose particle size is between 2 and 1000 μm.

8. Separating materials according to claim 7, wherein the particle size is between 3 and 300 μm.

9. Separating materials according to claim 1, wherein the support material is in the form of non-porous particles.

10. Separating materials according to claim 1, wherein the support material is in the form of porous particles having pore sizes between 2 and 300 nm.

11. Separating materials according to claim 10, wherein the pore sizes are between 5 and 200 nm.

12. Separating materials according to claim 1, wherein said at least one monomer unit which carries a charge is 3-sulfopropyl acrylate, 2-sulfoethyl acrylate, and 3-sulfopropyl methacrylate or 2-sulfoethyl methacrylate.

13. Separating materials according to claim 1, wherein in said at least one monomer unit having a charge is 2-acrylamido-2-methylpropanesulfonic acid (AMPS) or 2-acrylamidoethanesulfonic acid.

14. Separating materials according to claim 1, wherein in said at least one monomer unit having a charge is 2-(diethylaminoethyl)acrylate, 2-(dimethylaminoethyl)acrylate, 2-(dimethylaminopropyl)acrylate, 2-(diethylaminoethyl)methacrylate, 2-(dimethylaminoethyl)methacrylate or 3-(diethylaminopropyl)methacrylate.

15. Separating materials according to claim 1, wherein in said at least one monomer unit having a charge is 2-(diethylaminoethyl)acrylamide, 2-(dimethylaminoethyl)acrylamide, 3-(diethylaminopropyl)acrylamide, 2-(diethylaminoethyl)methacrylamide, 2-(dimethylaminoethyl)methacrylamide, or 3-(diethylaminopropyl)methacrylamide.

16. Separating materials according to claim 1, wherein in said at least one monomer unit having a charge is [2-(acryloxy)ethyl]trimethylammonium chloride or [2-(methacryloxy)ethyl]trimethylammonium chloride.

17. Separating materials according to claim 1, wherein in said at least one monomer unit having a charge is 2-(acryloylaminoethyl)trimethylammonium chloride, 3-(acryloylaminopropyl)trimethylammonium chloride, 2-(methacryloylaminoethyl)-trimethylammonium chloride or 3-(acryloylaminopropyl)trimethylammonium chloride.

18. A process for preparing separating materials according to claim 1, comprising:
grafting a copolymer onto a hydroxyl-containing surface of said support material by building up graft polymers from two or more recurring monomer units, where at least one of these recurring monomer units carries a charge and at least one of these recurring monomer units carries an uncharged group which carries mono- or dialkyl- and/or alkoxyethyl- or alkoxypropyl-substituted amide groups which are bonded to said hydroxyl-containing surface by chemical reaction, giving materials which are capable of binding charged substances by ionic interaction.

19. Separating materials according to claim 1, wherein in said at least one monomer unit having a charge is 2-acrylamido-2-methylpropanesulfonic acid and said at least one uncharged monomer unit of formula (1) is dimethylacrylamide.

20. Separating materials according to claim 1, wherein in said at least one monomer unit having a charge is 2-acrylamido-2-methylpropanesulfonic acid and said at least one uncharged monomer unit of formula (1) is methoxyethylacrylamide.

21. Separating materials according to claim 1, wherein in said at least one monomer unit having a charge is 2-acrylamidoethanesulfonic acid and said at least one uncharged monomer unit of formula (1) is dimethylacrylamide.

22. Separating materials according to claim 1, wherein in said at least one monomer unit having a charge is 2-(acryloxylaminoethyl)trimethylammomium chloride and said at least one uncharged monomer unit of formula (1) is dimethylacrylamide.

* * * * *

UNITED STATES PATENT AND TRADEMARK OFFICE
CERTIFICATE OF CORRECTION

PATENT NO.       : 8,673,988 B2                                                    Page 1 of 1
APPLICATION NO.  : 13/055983
DATED            : March 18, 2014
INVENTOR(S)      : Graalfs et al.

It is certified that error appears in the above-identified patent and that said Letters Patent is hereby corrected as shown below:

In the Claims

Claim 2, Column 17, line 17 reads "$R^3$ denotes $R^4$-$SO_3M$, $R^4$-COO, $R^4$-$NR^9R^{100}$r"
should read -- $R^3$ denotes $R^4$-$SO_3M$, $R^4$-COO, $R^4$-$NR^9R^{10}$ or --

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,673,988 B2
APPLICATION NO. : 13/055983
DATED : March 18, 2014
INVENTOR(S) : Graalfs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 298 days.

Signed and Sealed this

Twenty-ninth Day of September, 2015

Michelle K. Lee
*Director of the United States Patent and Trademark Office*